US009737680B2

(12) United States Patent
Hsiao et al.

(10) Patent No.: US 9,737,680 B2
(45) Date of Patent: Aug. 22, 2017

(54) HUMIDIFIER FOR RESPIRATORY APPARATUS

(71) Applicant: APEX MEDICAL CORP., New Taipei (TW)

(72) Inventors: Chia-Hsiang Hsiao, New Taipei (TW); Chih-Tsan Chien, New Taipei (TW); Ying-Chieh Hsu, New Taipei (TW); Ming-Cheng Chang, New Taipei (TW); Hsin-Wei Chen, New Taipei (TW); Wen-Bin Shen, New Taipei (TW); Shu-Chi Lin, New Taipei (TW); Yi-Chen Lu, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 446 days.

(21) Appl. No.: 14/459,972

(22) Filed: Aug. 14, 2014

(65) Prior Publication Data

US 2015/0059748 A1    Mar. 5, 2015

Related U.S. Application Data

(60) Provisional application No. 61/873,337, filed on Sep. 3, 2013.

(51) Int. Cl.
*A61M 16/16* (2006.01)
*A61M 16/14* (2006.01)
(Continued)

(52) U.S. Cl.
CPC .......... *A61M 16/109* (2014.02); *A61M 16/06* (2013.01); *A61M 16/16* (2013.01);
(Continued)

(58) Field of Classification Search
CPC .......... A61M 11/042; A61M 11/06; A61M 16/0057; A61M 16/0066; A61M 16/1075; A61M 16/109; A61M 16/125; A61M 16/142; A61M 16/16; A61M 16/162; A61M 16/167; A61M 16/168; A61M 2016/0021;
(Continued)

(56) References Cited

U.S. PATENT DOCUMENTS 3,617,698 A * 11/1971 Duncanson .......... A61M 11/041
128/909
3,806,102 A * 4/1974 Valenta ................. A61M 16/16
128/200.13
(Continued)

*Primary Examiner* — Annette Dixon
(74) *Attorney, Agent, or Firm* — Muncy, Geissler, Olds & Lowe, P.C.

(57) ABSTRACT

A humidifier for a respiratory apparatus includes a first cover, a second cover engaged with the first cover and a partition plate. The first cover defines an air inlet. The second cover defines a chamber configured to contain at least some amount of water. A heater is configured to heat the water to generate humidified air in the chamber. The partition plate is partly sandwiched between the first cover and the second cover. The partition plate defines an air outlet. Air input via the air inlet is humidified by being mixed with the humidified air and thereafter ejected through the air outlet. The air entering via the air inlet is divided by the partition plate into a plurality of flows having different flow velocities, thereby form a plurality of flow paths.

20 Claims, 11 Drawing Sheets

(51) Int. Cl.
*A61M 16/10* (2006.01)
*A61M 16/06* (2006.01)

(52) U.S. Cl.
CPC ............... *A61M 2205/123* (2013.01); *A61M 2205/3653* (2013.01); *A61M 2206/14* (2013.01)

(58) Field of Classification Search
CPC ...... A61M 2202/0208; A61M 2205/21; A61M 2205/3386; A61M 2205/3653; A61M 2205/42; A61M 2205/581; A62B 21/00; B01F 3/04; F22B 1/30; F24F 13/00; F24F 2006/008; F24F 6/025; H02H 11/001; Y10S 261/65; Y10T 137/8342; Y10T 403/59; Y10T 403/60; Y10T 403/608
USPC ............ 128/200.13, 200.21, 200.24, 203.12, 128/203.16, 203.17, 203.25, 203.26, 128/203.27, 204.13, 204.14, 204.17; 261/104, 113, 122.1, 139, 141, 142, 150, 261/154, 156, 57, 64.3, 66, 70, 72.1, 79.2
See application file for complete search history.

(56) References Cited

U.S. PATENT DOCUMENTS

| | | | | |
|---|---|---|---|---|
| 4,028,526 | A | * | 6/1977 | Schossow ............ H02H 11/001 128/203.27 |
| 5,564,415 | A | * | 10/1996 | Dobson ................. A61M 16/16 128/200.24 |
| 6,935,337 | B2 | * | 8/2005 | Virr ....................... A61M 16/16 128/203.16 |
| 2004/0055597 | A1 | * | 3/2004 | Virr ....................... A61M 16/16 128/203.12 |
| 2015/0054183 | A1 | * | 2/2015 | Chen ........................ B01F 3/04 261/150 |

* cited by examiner

HUMIDIFIER FOR RESPIRATORY APPARATUS

CROSS-REFERENCE TO RELATED APPLICATION

This application claims the benefit under 35 U.S.C. §119 (c) of U.S. Provisional Application No. 61/873,337, filed on Sep. 3, 2013, entitled "HUMIDIFIER for Respiratory Apparatus", the disclosure of which is incorporated by reference herein.

FIELD

The disclosure generally relates to a humidifier, and particularly relates to a humidifier for a respiratory apparatus.

BACKGROUND

A humidifier is a device for supplying breathable air to user. An air inlet of the humidifier communicates with a blower and an air outlet of the humidifier communicates with a breathing mask. Air from the blower is humidified in the humidifier and then passes to the breathing mask through an air delivery conduit. The humidifier generally includes a first cover, a second cover and a partition plate. The first cover defines the air inlet for air to enter and the air outlet for air to flow out. The second cover includes a chamber with some water. A heating plate is embedded in a bottom of the chamber to heat the water to generate humidified air. The air from the air inlet is humidified by mixing with the humidified air and passes out of the humidifier through the air outlet. The partition plate is located between the first cover and the second cover to prevent the water from entering the air inlet or the air outlet of the first cover. Traditionally, the partition plate is just a flat plate for preventing water in the second cover from entering the air inlet and the air outlet in the first cover. However, when air flows into the humidifier through the air inlet, a resonance phenomenon will occur in the single chamber of the humidifier and noise is thus generated. The noise generated from the resonance can be a disturbance to a user either awake or asleep. In addition, prior humidifiers did not provide flow with high humidity and thus it was uncomfortable for a user to breathe the air generated.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, like reference numerals designate corresponding parts throughout the several views.

DETAILED DESCRIPTION

An embodiment of a humidifier will now be described in detail below and with reference to the drawings.

Figure 1:
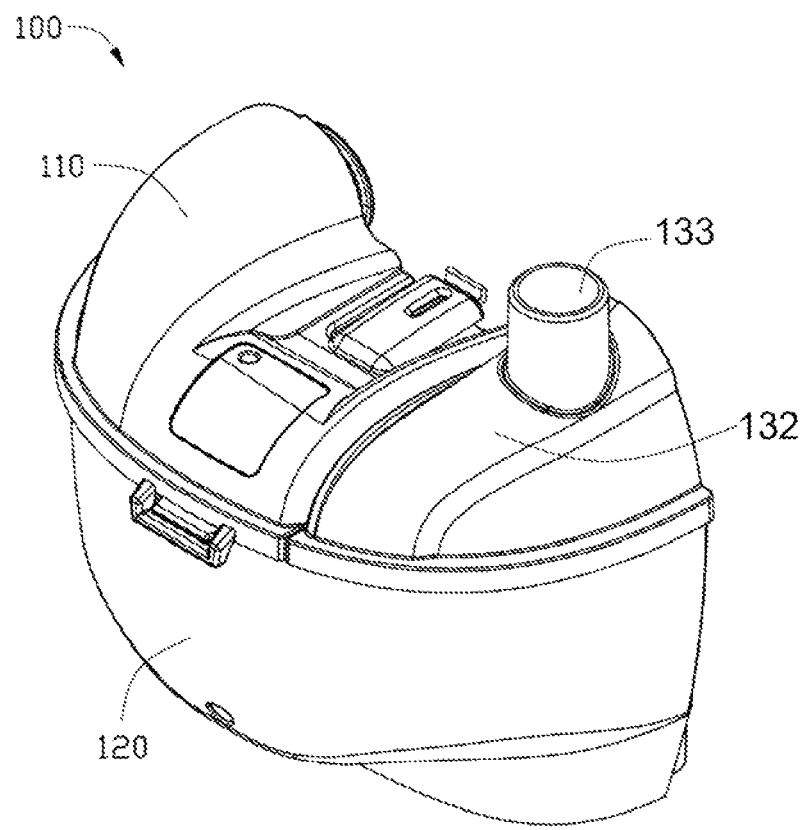
FIG. 1 is an isometric view of a humidifier in accordance with an embodiment of the present disclosure.
Figure 2:
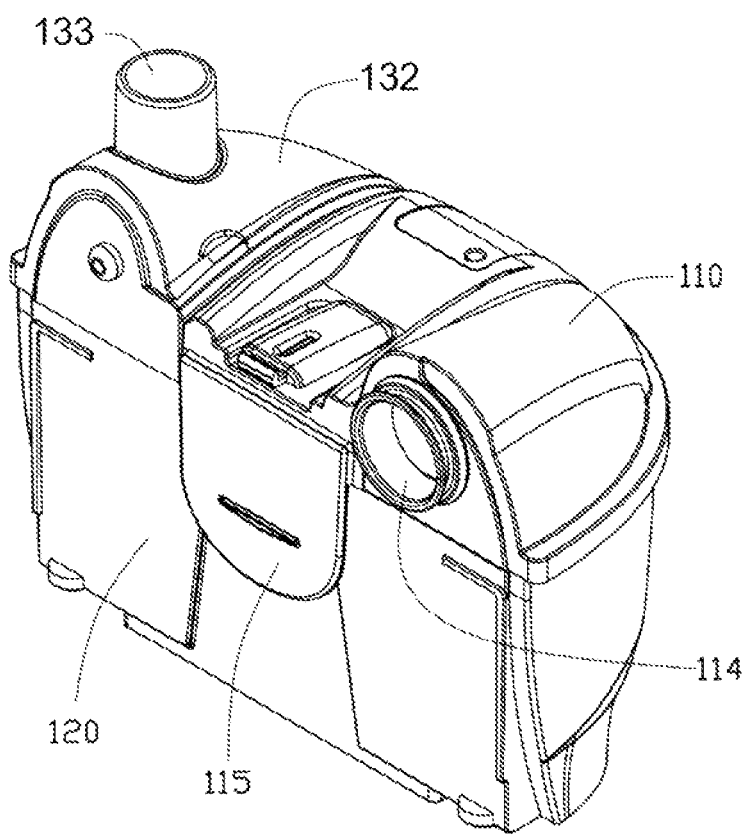
FIG. 2 is another isometric view of the humidifier in FIG. 1.
Figure 3:
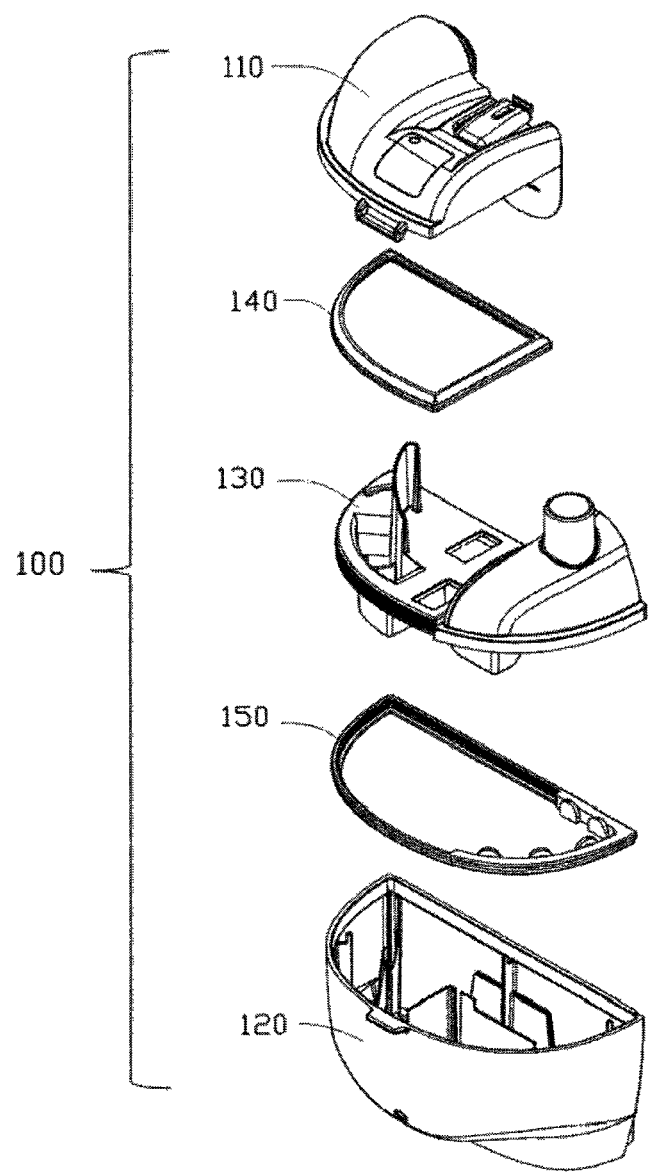
FIG. 3 is an exploded perspective view of the humidifier in FIG. 1.

Referring to FIGS. 1-3, a humidifier 100 in accordance with an embodiment is provided. The humidifier 100 includes a first cover 110, a second cover 120, a partition plate 130, a first gasket 140 and a second gasket 150.

Figure 4:
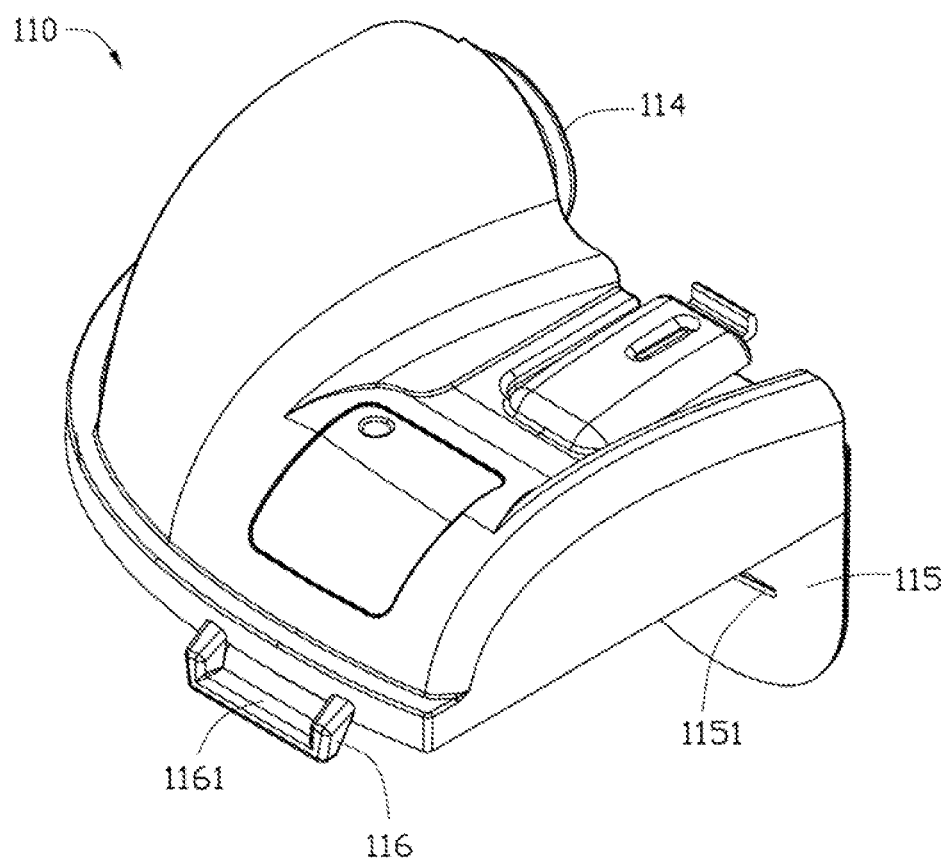
FIG. 4 is an isometric view of an first cover in FIG. 3.
Figure 5:
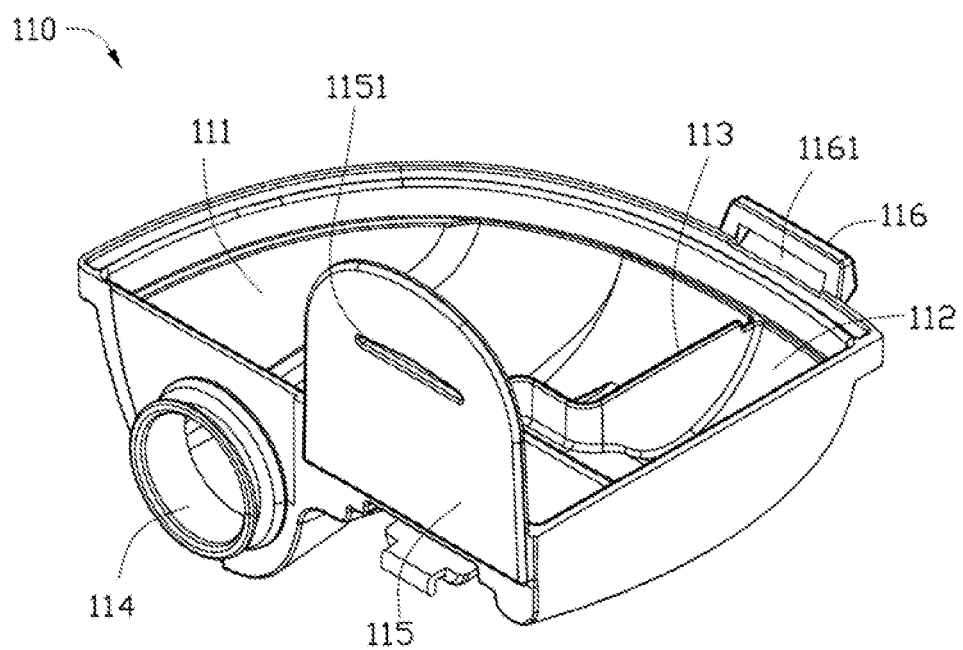
FIG. 5 is an inverted, isometric view of the first cover in FIG. 4.

Referring to FIGS. 4-5, the first cover 110 defines a first chamber 111 and a second chamber 112. The first chamber 111 is separated from the second chamber 112 by a first divider plate 113. When the first cover 110 is assembled with the partition plate 130, the first divider plate 113 abuts on, or contacts at least in part with, partition plate 130 and substantially separates the first chamber 111 from the second chamber 112. An air inlet 114 is defined at a lateral side of the first cover 110 and communicates with the first chamber 111. The air inlet 114 is configured to communicate with an air blower (not shown) and receive air from the air blower. The first cover 110 further includes a first engaging portion 115 and a second engaging portion 116. The first engaging portion 115 defines a first groove 1151, and the second engaging portion defines a second groove 1161. The first engaging portion 115 and the second engaging portion 116 are configured to connect the first cover 110 with the second cover 120. In one embodiment, the first chamber 111 is defined at the first side of the first cover 110 and the second chamber 112 is defined at the second side of the first cover 110. The second side of the first cover 110 has a curved shape.

Figure 6:
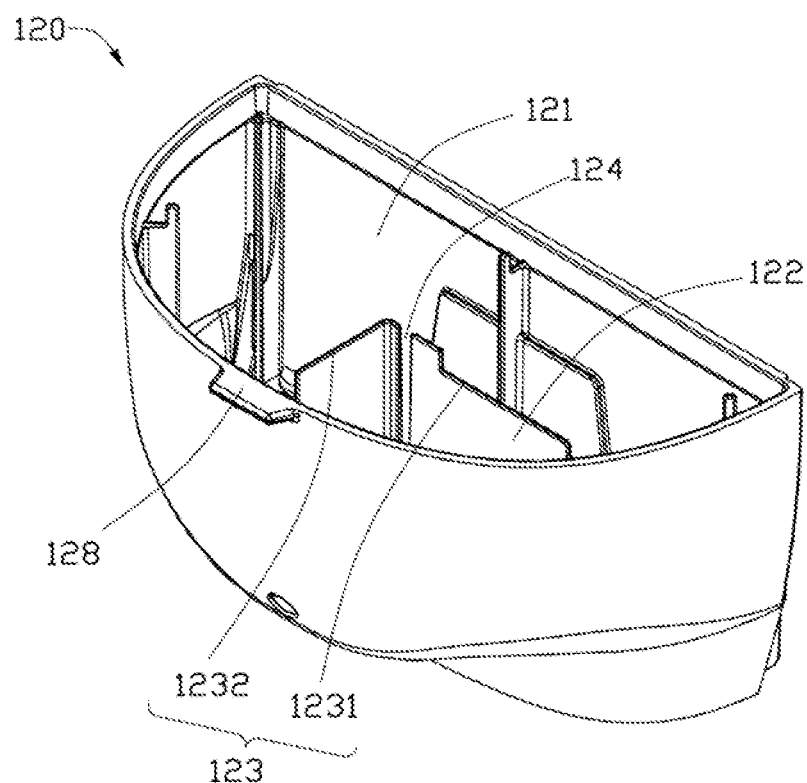
FIG. 6 is an isometric view of a second cover in FIG. 3.
Figure 7:
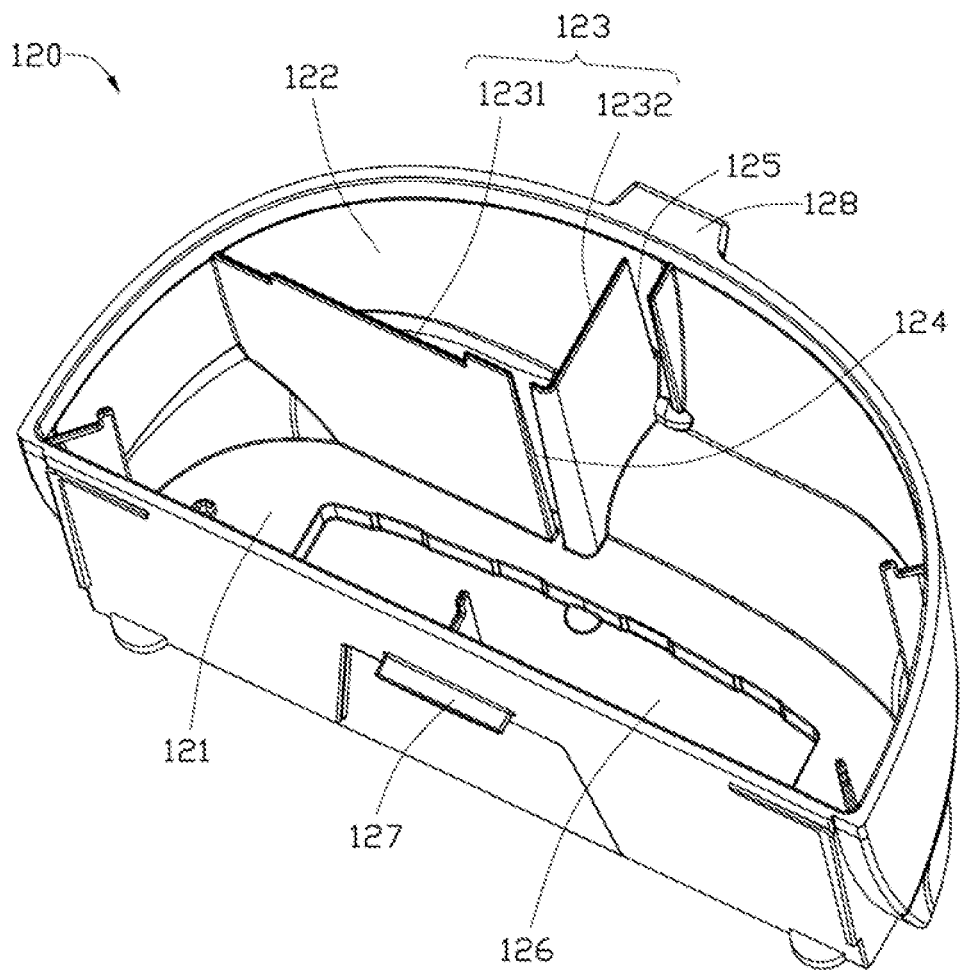
FIG. 7 is an isometric view of the second cover in FIG. 6, viewed in another perspective.

Referring to FIGS. 6-7, the second cover 120 defines a third chamber 121 and a fourth chamber 122. The third chamber 121 is separated from the fourth chamber 122 by a second divider plate 123. The third chamber 121 and the fourth chamber 122 can be filled with water. The second divider plate 123 defines a first aperture 124 and a second aperture 125 to communicate the third chamber 121 and the fourth chamber 122, thereby allowing the water to flow freely between the third chamber 121 and the fourth chamber 122. In this embodiment, the second divider plate 123 includes a first flat portion 1231 and a second flat portion 1232. The first flat portion 1231 is substantially perpendicular to the second flat portion 1232 to make the second divider plate 123 into an "L" shape. The second divider plate 123 can be in any shape which can provide the shape of the fourth chamber 122. The first aperture 124 is defined in the first flat portion 1231 in a position adjacent to the second flat portion 1232. The second aperture 125 is defined in the second flat portion 1232 in a position adjacent to an edge of the second cover 120. The second aperture 125 described here can be in any form which can provide the communication between the third chamber 121 and the fourth chamber 122. Alternatively, the second aperture 125 can be, but is not limited to, a slot, a through hole, an opening, or a filter. The second aperture 125 can employ the combination of the configuration described above and can be in plural form. The second cover 120 can be in one piece with the second divider plate 123 which may be made of plastic materials, or can be formed by assembling a plurality of plastic elements together. A bottom plate 126 of the second cover 120 can be configured to serve as a heat transfer medium. Preferably, the bottom plate 126 can be made of metal, which is configured to securely engage the second cover 120 to contain water without leakage. The bottom plate 126 can be made of plastic and is either in one piece with the second cover 120 or is an independent member. In one embodiment, the bottom plate 126 can be made of plastic material and further, on its outer surface, engaged with a metal cap. The bottom plate 126 is configured to transfer heat to the water in the second cover 120 to generate humidified air. In one embodiment, a heating mechanism is provided to heat the water to generate humidified air. In one embodiment, the heating mechanism can be a heating plate embedded or formed together in a bottom of the chamber to heat the water to generate humidified air. In another embodiment, the heating mechanism can be a bottom plate 126 made of heat conductive material capable of transferring heat into the water in the chamber. In another embodiment, the heating mechanism can be a heater configured to heat the water in the humidifier. The second cover 120 further includes a first protrusion 127 and a second protrusion 128 extending outwardly from the edge thereof. In assembling the first cover 110 with the second cover 120, the first protrusion 127 is engaged with the first groove 1151 in the first engaging portion 115, and the second protrusion 128 is engaged with the second groove 1161 in the second engaging portion 116. The engagement between the first cover 110 and the second cover 120 can employ different mechanisms which can provide secure or substantially secure, engagement. In other embodiments, the engagement can be, but is not limited to, a buckle engagement, a velcro strap or a securing strap, or the defined combination of the above.

Figure 8:
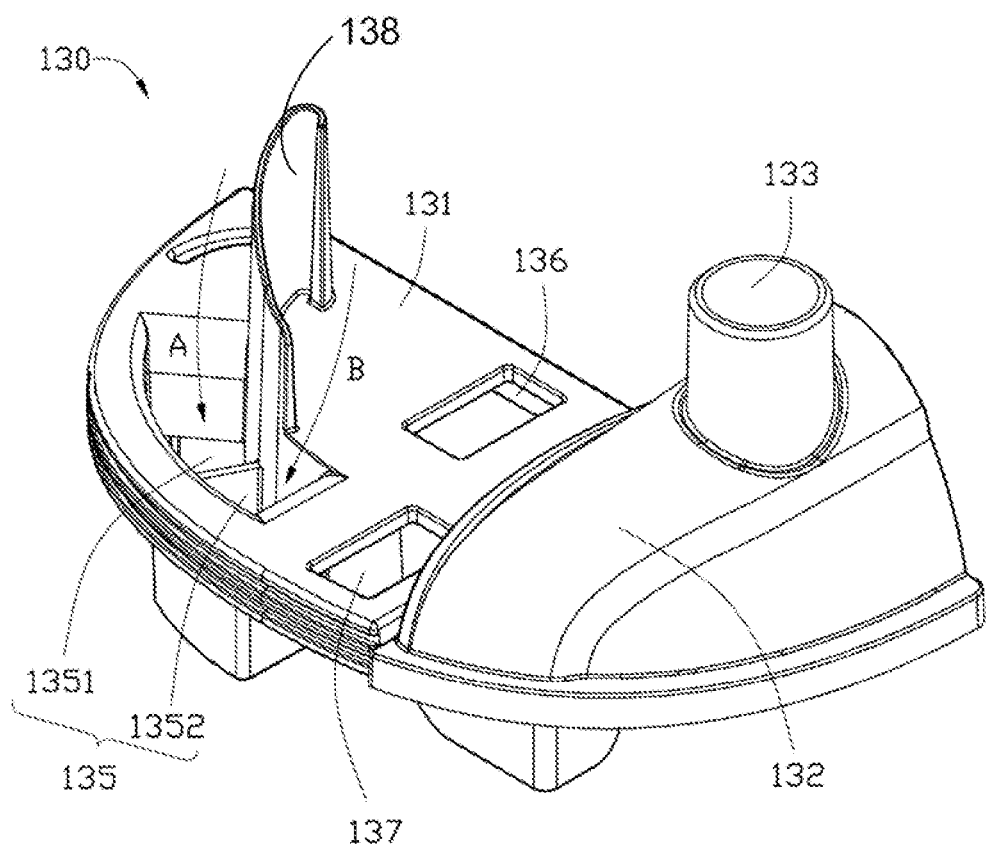
FIG. 8 is an isometric view of a partition plate in FIG. 3.
Figure 9:
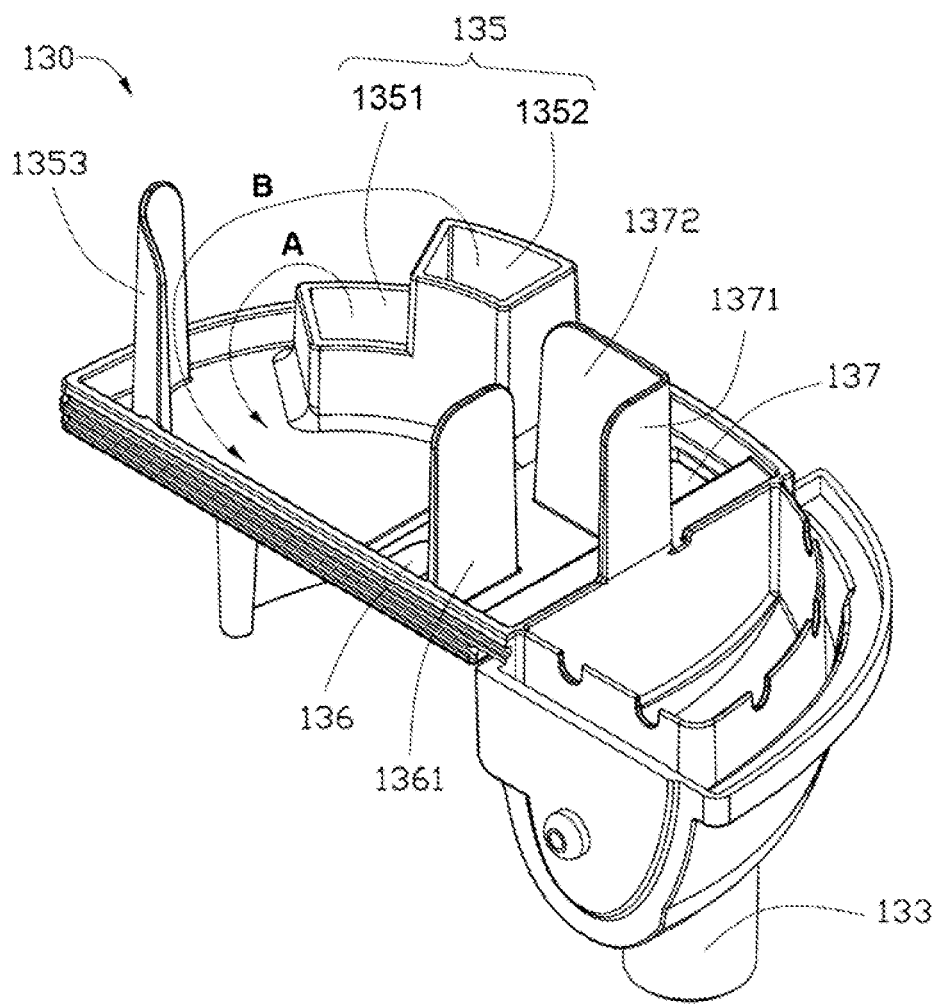
FIG. 9 is an inverted, isometric view of the partition plate in FIG. 8.
Figure 10:
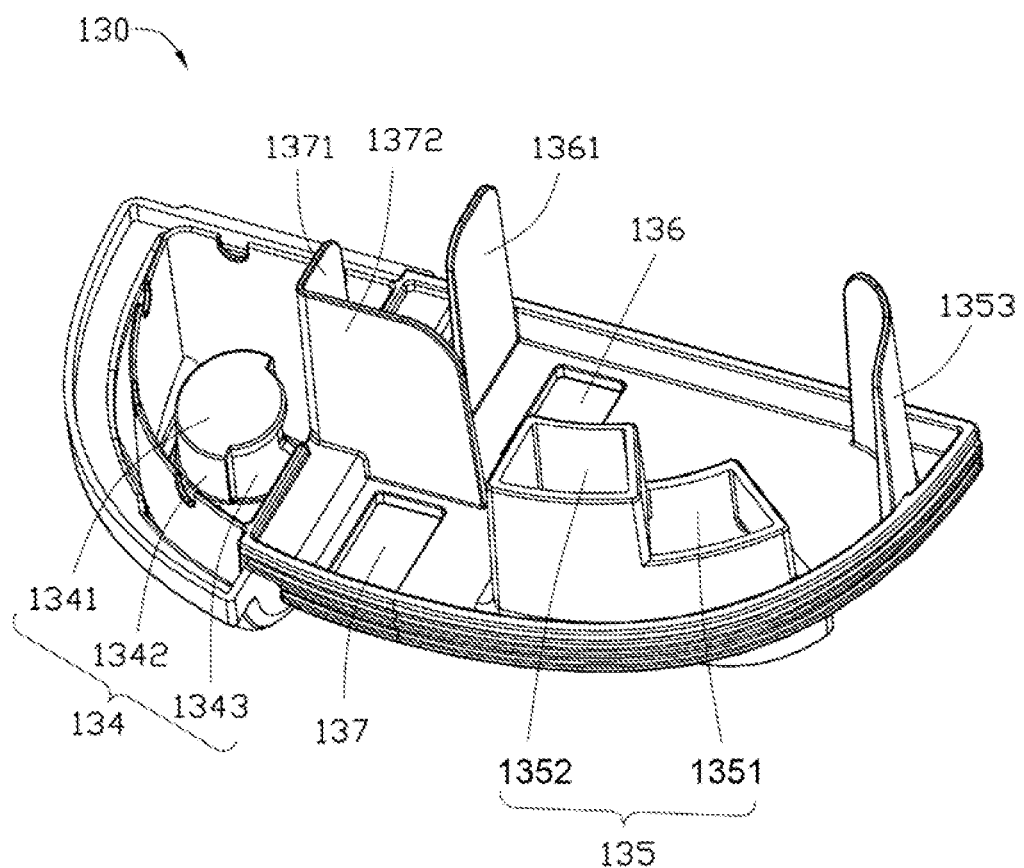
FIG. 10 is an inverted, isometric view of the partition plate in FIG. 8, viewed in another perspective.

Referring to FIGS. 8-10, the partition plate 130 includes a main body 131 and a side body 132 formed at one side of the main body 131. The side body 132 defines an air outlet 133 on an upper portion thereof. In this embodiment, the upper portion of the side body 132 defines a chamber (not shown in the figures) which can contain air so as to provide a path for air to flow to the air outlet 133. The air outlet 133 communicates with the third chamber 121 and the fourth chamber 122 of the second cover 120. A blocking member 134 is formed under the air outlet 133. The blocking member 134 includes a bottom wall 1341 and a side wall 1342. The bottom wall 1341 and the side wall 1342 cooperatively define a sectoring hole 1343 to communicate the air outlet 133 with the third chamber 121 and the fourth chamber 122. In this embodiment, the bottom wall 1341 is horizontal and the side wall 1342 is located in the area between the bottom wall 1341 and the upper portion of the side body 132. When humidified air is condensed on the upper portion of the side body 132 near the air outlet 133, the bottom wall 1341 and the side wall 1342 of the blocking member 134 can prevent water from entering the sectoring hole 1343 and passing to a breathing mask or an air delivery conduit through the air outlet 133. The blocking member 134 can be in any shape or any form which can reduce or block liquid from entering the conduit. The main body 131 defines a first opening 135, a second opening 136 and a third opening 137. The first opening 135 is located in a position away from the air outlet 133. The second opening 136 and the third opening 137 are located in the area between the first opening 135 and the air outlet 133. When the partition plate 130 is assembled with the first cover 110, the first divider plate 113 abuts on or contacts the main body 131 and separates the first opening 135 from the second opening 136 and the third opening 137. The first chamber 111 is in communication with the third chamber 121 via the first opening 135. The third chamber 121 is in communication with the second chamber 112 via the second opening 136. The second chamber 112 is in communication with the fourth chamber 122 via the third opening 137. The first opening 135 comprises a first portion 1351 and a second portion 1352. The first portion 1351 and the second portion 1352 extend downwardly from the main body 131 so as to form two open ended well-like portions. An extending length of the first portion 1351 is less than an extending length of the second portion 1352. In one embodiment, an air guiding plate 138 is located beside the first opening 135 and extends upwardly from the main body 131. When air enters into the humidifier 100 from the air inlet 114, the air is divided into two different parts by the air guiding plate 138 (hereinafter "Flow A" and "Flow B" respectively). Flow A travels between an outer edge of the first cover 110 and the air guiding plate 138, and enters the third chamber 121 through the first portion 1351 of the first opening 135. Flow B travels between the air guiding plate 138 and the first divider plate 113, and enters the third chamber 121 through the second portion 1352 of the first opening 135. The second opening 136 and the third opening 137 can have, but is not limited to, a rectangular structure. The main body 131 further comprises a first air guiding plate 1353, a second air guiding plate 1361, a third air guiding plate 1371 and a supporting plate 1372 extending downwardly from the main body 131. The first air guiding plate 1353 is located at one side of the first portion 1351 away from the second portion 1352. In one embodiment, the first air guiding plate 1353 is curved outwardly away from the third chamber 121. The second air guiding plate 1361 is located at one side of second opening 136 adjacent to the sectoring hole 1343 of the blocking member 134. The third air guiding plate 1371 is located at one side adjacent to the third opening 137. The supporting plate 1372 is located between the second opening 136 and the third opening 137, and directly connected with the third air guiding plate 1371. The supporting plate 1372 is configured to support the third air guiding plate 1371. When the partition plate 130 is assembled with the second cover 120, the supporting plate 1372 abuts on or contacts the second divider plate 123. In another embodiment, the supporting plate 1372 can also be located adjacent to the second divider plate 123. It is to be noted that the supporting plate 1372 can be left out if desired. Still, the plates described above can be in one piece with the partition plate 130 or can be separate members that can be securely attached to the relative position described.

In operation, air entering the humidifier 100 is divided into Flow A and Flow B. Flow A travels along one air channel between the outer edge of the first cover 110 and the air guiding plate 138 and enters the third chamber 121 through the first portion 1351 of the first opening 135. Flow B travels along another air channel between the air guiding plate 138 and the first divider plate 113 and enters through the third chamber 121 through the second portion 1352 of the first opening 135. As illustrated in FIG. 9, since the extending length of the first portion 1351 is shorter than that of the second portion 1352, Flow A passing through the first portion 1351 has a flow velocity higher than Flow B passing through the second portion 1352. According to Bernoulli's law, an increase in the speed of the flow occurs simultaneously with a decrease in pressure. Therefore, Flow A will have a lower pressure than Flow B. Since it is a natural phenomenon to have a high pressure air to flow toward a low pressure air, Flow B will move toward Flow A and thus create a certain path of air flow. When Flow B flows toward Flow A, both flows reach the first air guiding plate 1353 and the curved first air guiding plate 1353 can guide the flows. Since the first air guiding plate 1353 is curved, the flows (which may be Flow A, Flow B or the mixed flow of both) can follow the direction given by the curvature of the first air guiding plate 1353 and thus create a rotation of the flows within the third chamber 121. Therefore, a traveling path of air in the third chamber 121 is extended and the rotating air will be better mixed with humidified air in the third chamber 121. When the rotating air reaches the second air guiding plate 1361, the rotating air will enter the second chamber 112 of the first cover 110 through the second opening 136. Since the rotating air continues to enter the second chamber 112 of the first cover 110 through the second opening 136, air in the second chamber 112 will enter the fourth chamber 122 of the second cover 120 through the third opening 137 and become mixed with humidified air in the fourth chamber 122 again. The air in the fourth chamber 122 will then enter the sectoring hole 1343 of the blocking member 134 and move out of the humidifier 100 from the air outlet 133. When the rotating air reaches the third air guiding plate 1371, the air will travel along an air channel between the second air guiding plate 1361 and the third air guiding plate 1371, and directly enter the sectoring hole 1343 of the blocking member 134 and exit the humidifier 100 from the air outlet 133.

In the humidifier 100 described above, air entering the air inlet 114 is divided into Flow A and Flow B by the air guiding plate 138. After passing through the first portion 1351 and the second portion 1352 of the first opening 135 respectively, Flow A and Flow B will have different flow velocities. Flow A and Flow B with different flow velocities will collide with the first air guiding plate 1353, the second air guiding plate 1361, and the third air guiding plate 1371 to generate sounds with different frequencies. Therefore, a resonance phenomenon in the second cover 120 is mitigated or avoided, and noise generated by the humidifier 100 is reduced. Furthermore, the first air guiding plate 1353 guides Flow A and Flow B with different flow velocities to rotate. The rotating air in the third chamber 121 will be better mixed with the humidified air, thereby increasing humidity of the flows.

The humidifier 100 can further include a first gasket 140 and a second gasket 150. The first gasket 140 is formed between the first cover 110 and the partition plate 130. The second gasket 150 is formed between the second cover 120 and the partition plate 130. The first gasket 140 and the second gasket 150 are configured to prevent water or air from leaking out of the humidifier 100. It is to be noted that the mechanism used to secure the engagement of the humidifier assembly to prevent water or air flow leakage can be employed in different ways.

Figure 11:
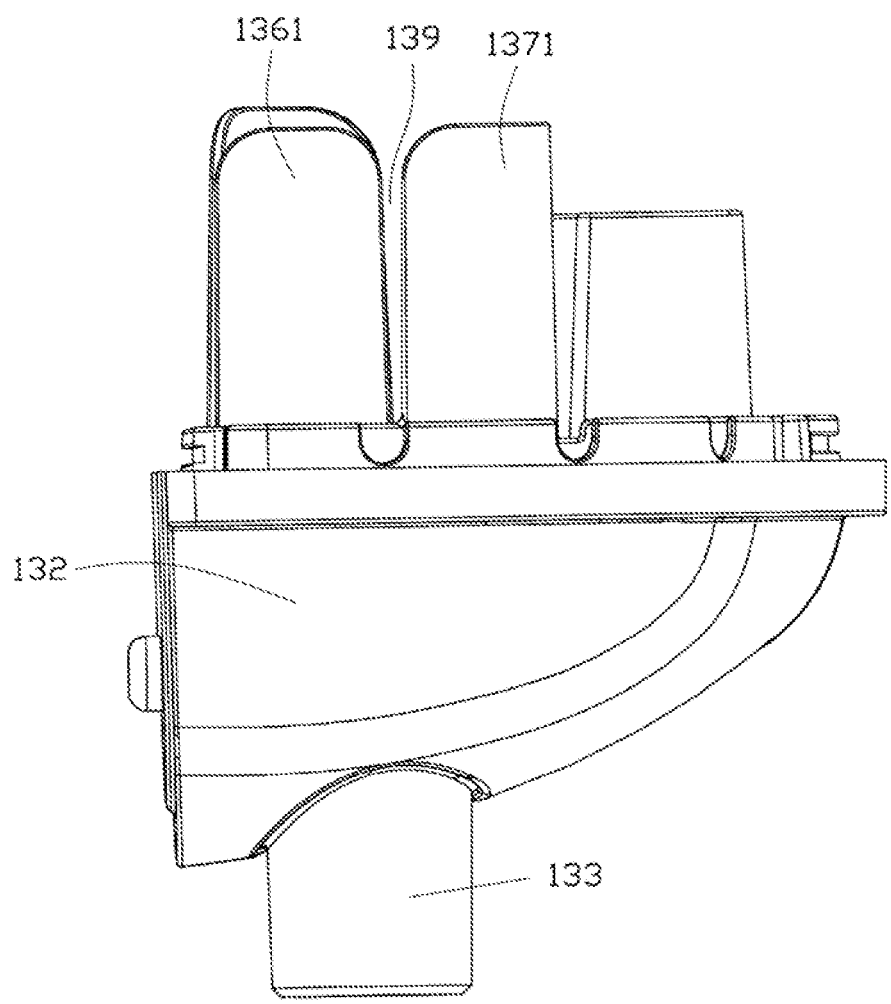
FIG. 11 is an inverted, isometric view of the partition plate in FIG. 8, viewed in yet another perspective.

In addition, the second air guiding plate 1361 is substantially parallel to the third air guiding plate 1371. As shown in FIG. 11, seen from the lateral side of the partition plate 130, a gap 139 is formed between the second air guiding plate 1361 and the third air guiding plate 1371. A portion of the flow in the third chamber 121 can pass through the gap 139 to the air outlet 133. The second air guiding plate 1361 and the third air guiding plate 1371 can extend the flow path and disturb the flows in the third chamber 121. This further helps reduce spills of the contained water by mitigating the blowing force and thus reducing the possibility of spills entering the conduit and the mask. The width of the gap 139 may influence the phenomena described above. In this embodiment, the gap 139 between the second air guiding plate 1361 and the third air guiding plate 1371 has a width in a range from 1 mm to 8 mm. Preferably, the gap 139 between the second air guiding plate 1361 and the third air guiding plate 1371 has a width about 2 mm. It is to be noted that the gap 139 may be employed in different shape. As shown in FIG. 11, the gap 139 can be formed in a slight V shape.

It is to be further understood that even though numerous characteristics and advantages of the present embodiments have been set forth in the foregoing description, together with details of the structures and functions of the embodiments, the disclosure is illustrative only, and changes may be made in detail, including in matters of shape, size, and arrangement of parts within the principles of the disclosure to the full extent indicated by the broad general meaning of the terms in which the appended claims are expressed.

What is claimed is:

1. A humidifier for a respiratory apparatus, the humidifier comprising:
   a first cover defining an air inlet;
   a second cover engaged with the first cover, the second cover defining a chamber configured to contain at least some amount of water;
   a heating mechanism provided to generate humidified air in the chamber; and
   a partition plate at least partly sandwiched between the first cover and the second cover, the partition plate defining an air outlet, wherein air input via the air inlet is humidified by being mixed with the humidified air and thereafter ejected through the air outlet; and
   wherein air entering via the air inlet is divided by the partition plate into a plurality of flows having different flow velocities, thereby forming a plurality of flow paths.

2. The humidifier for respiratory apparatus of claim 1, wherein the partition plate comprises a main body and a side body formed at one side of the main body, the air outlet being defined at an upper portion of the side body, the main body being sandwiched between the first cover and the second cover.

3. The humidifier for respiratory apparatus of claim 2, wherein the main body defines a first opening located in a position away from the air outlet, the first opening comprising a first portion and a second portion extending downwardly from the main body toward the second cover, an extending length of the first portion being less than that of the second portion.

4. The humidifier for respiratory apparatus of claim 3, wherein an air guiding plate is located beside the first opening and extends upwardly from the main body toward the first cover, the air from the air inlet being divided into two different parts by the air guiding plate, thereby the two different parts respectively passing through the first portion and the second portion to form the flows having different flow velocities.

5. The humidifier for respiratory apparatus of claim 4, wherein the first cover defines a first chamber and a second chamber, the first chamber being separated from the second chamber by a first divider plate, the first divider abutting on the main body when the first cover being assembled with the partition plate, the air inlet being defined at a lateral side of the first cover and communicated with the first chamber.

6. The humidifier for respiratory apparatus of claim 5, wherein the first chamber is defined at a first side of the first cover and the second chamber is defined at a second side of the first cover, the second side of the first cover having a curved shape for user handholding.

7. The humidifier for respiratory apparatus of claim 5, wherein the chamber of the second comprises a third chamber and a fourth chamber, the third chamber being separated from the fourth chamber by a second divider plate, the second divider plate defining at least one aperture to communicate the third chamber and the fourth chamber.

8. The humidifier for respiratory apparatus of claim 7, wherein a blocking member is formed under the air outlet, the blocking member comprising a bottom wall and a sidewall, the bottom wall and the side wall cooperatively defining a sectoring hole to communicate the air outlet with the third chamber and the fourth chamber.

9. The humidifier for respiratory apparatus of claim 8, wherein the bottom wall is horizontal and the side wall is located in the area between the bottom wall and the upper portion of the side body.

10. The humidifier for respiratory apparatus of claim 7, wherein the second divider plate comprises a first flat portion and a second flat portion, the second divider plate defining two apertures, one aperture being defined in the first flat portion in a position adjacent to the second flat portion, the other aperture being defined in the second flat portion in a position adjacent to an edge of the second cover.

11. The humidifier for respiratory apparatus of claim 7, wherein the main body further comprises a first air guiding plate extending downwardly from the main body toward the second cover, the first air guiding plate being located at one side of the first portion away from the second portion, the first air guiding plate being curved outwardly away from the third chamber, the flows passing through the first portion and the second portion with different flow velocities reaching the first air guiding plate, the flows following a direction given by the first air guiding plate and creating a rotation of the flows within the third chamber.

12. The humidifier for respiratory apparatus of claim 11, wherein the main body further defines a second opening and a third opening, the second opening and the third opening being located in the area between the first opening and the air outlet, the first divider plate separating the first opening from the second opening and the third opening, the third chamber being in communication with the second chamber via the second opening, the second chamber being in communication with the fourth chamber via the third opening, part of the flows from the first air guiding plate entering the second chamber of the first cover through the second opening, and thereby entering the fourth chamber of the second cover through the third opening and becoming mixed with humidified air in the fourth chamber.

13. The humidifier for respiratory apparatus of claim 12, wherein the main body further comprises a second air guiding plate and a third air guiding plate extending downwardly from the main body toward the second cover, the second air guiding plate being located at one side of the second opening adjacent to the sectoring hole of the blocking member, the third air guiding plate being located at one side adjacent to the third opening, part of the flows from the first air guiding plate traveling along an air channel between the second air guiding plate and the third air guiding plate, and directly entering the sectoring hole of the blocking member and moving out of the humidifier from the air outlet.

14. The humidifier for respiratory apparatus of claim 13, wherein the main body further comprises a supporting plate extending downwardly from the main body, the supporting plate being located between the second opening and the third opening and directly connected with the third air guiding plate to support the third air guiding plate, the supporting plate abutting on the second divider plate.

15. The humidifier for respiratory apparatus of claim 13, wherein a gap is formed between the second air guiding plate and the third air guiding plate, part of the flows in the third chamber passing through the gap to the air outlet, the second air guiding plate and the third air guiding plate extending the flow path and disturbing the flows in the third chamber.

16. The humidifier for respiratory apparatus of claim 1, wherein the second cover comprises a bottom plate, the bottom plate being configured to heat the water to generate the humidified air.

17. The humidifier for respiratory apparatus of claim 1, wherein the second cover comprises a first protrusion extending outwardly from an edge thereof, the first cover comprising a first engaging portion corresponding to the first protrusion, the first engaging portion defining a first groove, the first protrusion being engaged with the first groove in the first engaging portion to connect the second cover and the first cover.

18. The humidifier for respiratory apparatus of claim 1, wherein the humidifier further comprises a first gasket and a second gasket, the first gasket being formed between the first cover and the partition plate, the second gasket being formed between the second cover and the partition plate.

19. A humidifier assembly, comprising:
a heating mechanism, the heating mechanism being configured to heat water to generate humidified air in the humidifier assembly;
a humidifier, the humidifier comprising
a first cover defining an air inlet;
a second cover engaged with the first cover, the second cover defining a chamber configured to contain at least some amount of water;
a partition plate at least partly sandwiched between the first cover and the second cover, the partition plate defining an air outlet, wherein air input via the air inlet is humidified by mixing with the humidified air and thereafter ejected through the air outlet; and
wherein the partition plate comprising a first opening located in a position away from the air outlet and an air guiding plate upwardly extending toward the first cover, the first opening comprising a first portion and a second portion extending downwardly toward the second cover, the first portion and the second portion having different extending length, the air from the air inlet being divided into two different parts by the air guiding plate to form two flow paths, flows of one flow path entering the first portion and flows of the other flow path entering the second portion.

20. A humidifier assembly, comprising:
a heating mechanism, the heating mechanism being configured to heat water to generate humidified air in the humidifier assembly;
a humidifier, the humidifier comprising
a first cover defining an air inlet;
a second cover engaged with the first cover, the second cover defining a chamber configured to contain at least some amount of water;
a partition plate at least partly sandwiched between the first cover and the second cover, the partition plate defining an air outlet, wherein air input via the air inlet is humidified by mixing with the humidified air; and
a first gasket and a second gasket, the first gasket being formed between the first cover and the partition plate, the second gasket being formed between the second cover and the partition plate.

* * * * *